(12) United States Patent
Zhu

(10) Patent No.: US 7,241,771 B2
(45) Date of Patent: Jul. 10, 2007

(54) OXEPANE ISOMER OF 42-O-(2-HYDROXY)ETHYL-RAPAMYCIN

(75) Inventor: Tianmin Zhu, Monroe, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/359,166

(22) Filed: Feb. 22, 2006

(65) Prior Publication Data

US 2006/0199834 A1    Sep. 7, 2006

Related U.S. Application Data

(60) Provisional application No. 60/659,378, filed on Mar. 7, 2005.

(51) Int. Cl.
*C07D 498/18* (2006.01)
*A61K 31/435* (2006.01)

(52) U.S. Cl. .................... 514/291; 540/456

(58) Field of Classification Search ........... 540/456; 514/291
See application file for complete search history.

(56) References Cited

U.S. PATENT DOCUMENTS

| 5,221,740 | A  | 6/1993  | Hughes       |
|-----------|----|---------|--------------|
| 5,344,833 | A  | 9/1994  | Hughes       |
| 6,277,983 | B1 | 8/2001  | Shaw et al.  |
| 6,331,547 | B1 | 12/2001 | Zhu et al.   |
| 6,399,625 | B1 | 6/2002  | Zhu          |
| 6,432,973 | B1 | 8/2002  | Zhu et al.   |
| 6,440,991 | B1 | 8/2002  | Zhu et al.   |
| 6,511,986 | B2 | 1/2003  | Zhang et al. |
| 6,670,355 | B2 | 12/2003 | Azrolan et al. |
| 6,677,357 | B2 | 1/2004  | Zhu et al.   |
| 6,680,330 | B2 | 1/2004  | Zhu et al.   |

FOREIGN PATENT DOCUMENTS

| EP | 0509795 A2    | 10/1992 |
| EP | 0649659 A1    | 4/1995  |
| EP | 0781776 A2    | 7/1997  |
| WO | WO-92/05179 A1| 4/1992  |
| WO | WO-92/21341 A1| 12/1992 |
| WO | WO-94/09010 A1| 4/1994  |
| WO | WO-2005/010010 A | 2/2005 |

OTHER PUBLICATIONS

Communication- International Search Report in International Application No. PCT/US2006/006125, mailed Jun. 26, 2006.

*Primary Examiner*—Bruck Kifle
(74) *Attorney, Agent, or Firm*—Howson & Howson LLP; Arnold S. Milowsky

(57) ABSTRACT

The invention provides a purified oxepane isomer of 42-O-(2-hydroxy)ethyl-rapamycin (SDZ-RAD Isomer C), a chemical process for its preparation, as well as pharmaceutical compositions and packs containing SDZ-RAD Isomer C and methods for its use as an immunosuppressive, anti-inflammatory, antifungal, antiproliferative and antitumor agent.

15 Claims, No Drawings

OXEPANE ISOMER OF 42-O-(2-HYDROXY)ETHYL-RAPAMYCIN

CROSS-REFERENCE TO RELATED APPLICATIONS

This application claims the benefit under 35 USC 119(e) of prior U.S. Provisional Patent Application No. 60/659,378, filed Mar. 7, 2005.

BACKGROUND OF THE INVENTION

This invention relates to a novel oxepane isomer of 42-O-(2-hydroxy)ethyl-rapamycin, a process for its preparation, and its use in treating, preventing or inhibiting transplant rejection, graft vs. host disease, autoimmune diseases, inflammatory diseases, adult T cell leukemia/lymphoma, solid tumors, fungal infections, and hyperproliferative vascular disorders, among others.

The structure and synthesis of 40-O-(2-hydroxy)ethyl rapamycin, also known as SDZ-RAD or RAD-666, is described in U.S. Pat. No. 5,665,772 (Cottens, et al.) and International Patent Publication No. WO 94/09010. When prepared according to U.S. Pat. No. 5,665,772, SDZ-RAD exists as a mixture containing about 95 wt % of Isomer B and 30 wt % of Isomer C (the oxepane isomer).

40-O-(2-hydroxy)ethyl rapamycin is now known as 42-O-(2-hydroxy)ethyl rapamycin, due to a change in numbering convention. SDZ-RAD is an analog of rapamycin, which is a macrocyclic triene antibiotic produced naturally by *Streptomyces hygroscopicus*.

Rapamycin has been found useful in an array of applications based on its antitumoral and immunosuppressive effects. Uses include preventing or treating systemic lupus erythematosis, pulmonary inflammation, insulin dependent diabetes mellitus, smooth muscle cell proliferation and intimal thickening following vascular surgery, adult T-cell leukemia/lymphoma, and ocular inflammation. Rapamycin and rapamycin derivatives, including SDZ-RAD, continue to be studied for treatment of these and other conditions.

SUMMARY OF THE INVENTION

The invention provides a purified oxepane isomer of 42-O-(2-hydroxy)ethyl rapamycin (SDZ-RAD), known as SDZ-RAD Isomer C.

In another aspect, the invention provides a chemical process for preparing purified SDZ-RAD Isomer C from SDZ-RAD.

In another aspect, the invention provides for pharmaceutical compositions containing purified SDZ-RAD Isomer C, for use in treating, inhibiting, and preventing transplant rejection, graft vs. host disease, autoimmune diseases, inflammatory diseases, adult T cell leukemia/lymphoma, solid tumors, fungal infections, and hyperproliferative vascular disorders, among other diseases and disorders, in a mammal in need thereof.

In another aspect, the invention provides for use of purified SDZ-RAD Isomer C in preparing a medicament useful for treating, inhibiting, and preventing transplant rejection, graft vs. host disease, autoimmune diseases, inflammatory diseases, adult T cell leukemia/lymphoma, solid tumors, fungal infections, and hyperproliferative vascular disorders, among other diseases and disorders, in a mammal in need thereof.

In yet another aspect, the invention provides a pharmaceutical kit or pack containing a course of treatment for transplant rejection, graft vs. host disease, autoimmune diseases, inflammatory diseases, adult T cell leukemia/lymphoma, solid tumors, fungal infections, and hyperproliferative vascular disorders, among other diseases and disorders, for an individual mammal, comprising a container having purified SDZ-RAD Isomer C in unit dosage form.

DETAILED DESCRIPTION OF THE INVENTION

The invention provides a purified oxepane isomer of 42-O-(2-hydroxy)ethyl rapamycin ("SDZ-RAD"), having the following structure:

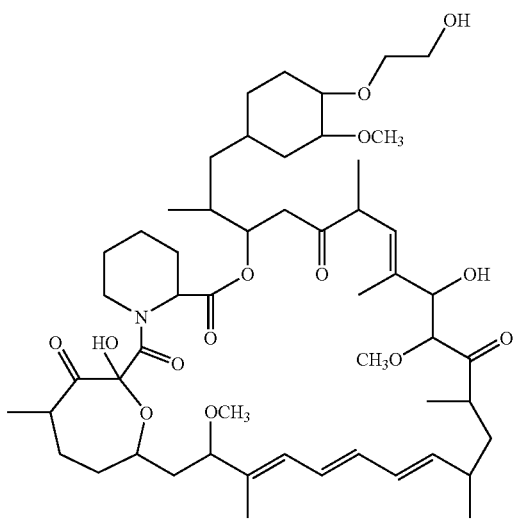

which may also be described by the formula: 1,17-dihydroxy-11-{2-[4-(2-hydroxy-ethoxy)-3-methoxy-cyclohexyl]-1methyl-ethyl}-18,29-dimethoxy-14,16,20,22,28,34-hexamethyl-10,36-dioxa-3-aza-tricyclo[29.4.1.0~3,8]hexatriaconta-15,23,25,27-tetraen-2,9,13,19,35-pentaone.

As used here, the term "SDZ-RAD Isomer C" means a compound having the preceding formula.

As used herein, the term "purified SDZ-RAD Isomer C" means a compound having the preceding formula (i.e., SDZ-RAD Isomer C) and having a purity of greater than 90 wt %, or greater than 95 wt %, 98 wt % or 99 wt %.

Also provided by the invention is a chemical process for preparing purified SDZ-RAD Isomer C from SDZ-RAD. SDZ-RAD Isomer C exists in equilibrium with SDZ-RAD Isomer B. Under conditions described herein, the equilibrium may be driven from the greatly favored Isomer B state to the Isomer C state, as summarized in Scheme I below. The preparation of SDZ-RAD (42-O-(2-hydroxy)ethyl rapamycin) is described (under its previous name of 40-O-(2-hydroxy)ethyl rapamycin) in U.S. Pat. No. 5,665,772 (Cottens, et al.). The conversion of SDZ-RAD Isomer B to SDZ-RAD Isomer C through an intermediate may be accomplished in a mixture of aqueous buffer and organic solvent in the range of about pH 4 to pH 10. In another embodiment, the aqueous buffer has a pH of from about 4 to 10, 5 to 9, 6 to 9, 7 to 9, or 7.5 to 8.5. In a further embodiment, the aqueous buffer has a pH of about 8.5.

Scheme I.
Conversion from SDZ-RAD to SDZ-RAD Isomer C through an Intermediate

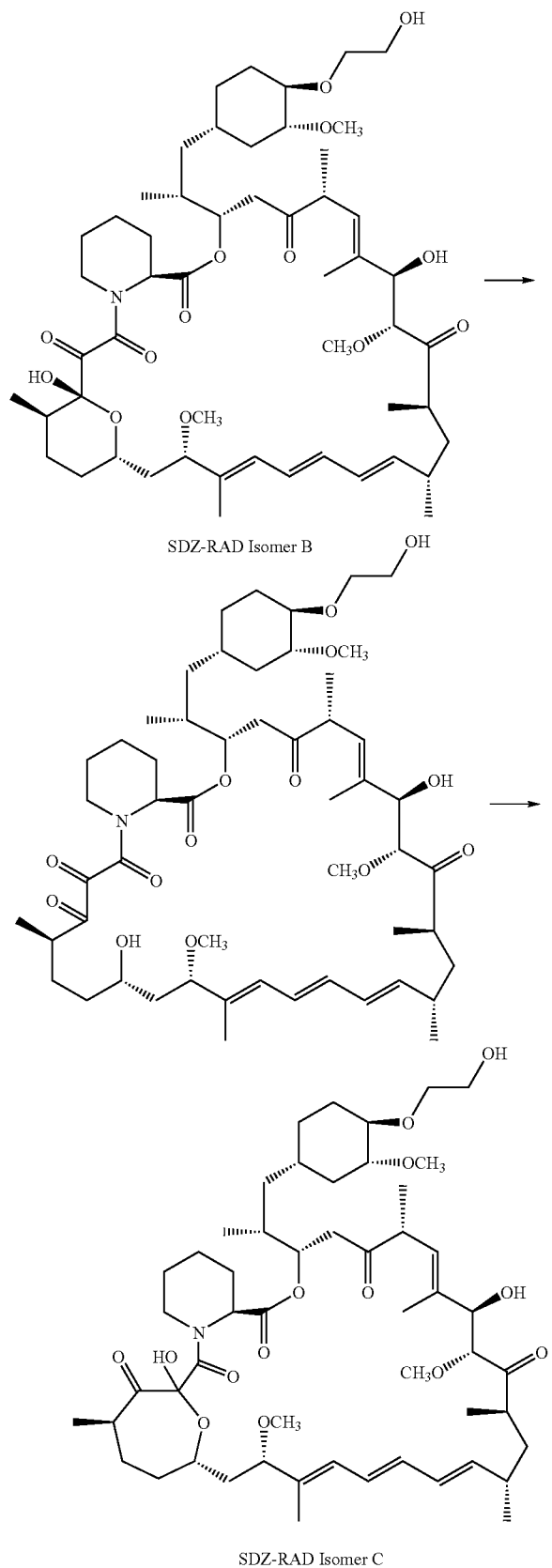

In one embodiment, the aqueous buffer is triethylammonium acetate (TEAA). In other embodiments, any suitable aqueous buffer may be readily selected by one of skill in the art, including, but not limited to, phosphate buffered saline, and water with sodium citrate buffer. In one embodiment, the organic solvent is a polar aprotic solvent, i.e., a solvent that has a molecular dipole but whose hydrogen atoms are not bonded to oxygen or nitrogen, or a dipolar aprotic solvent, i.e., a solvent that has a zero molecular dipole and whose hydrogen atoms are not bonded to oxygen or nitrogen, but has charges on individual atoms. In one embodiment, the organic solvent is acetonitrile (H—CO—N(CH$_3$)$_2$) or 1,4-dioxane (commonly referred to as dioxane). In another embodiment, the organic solvent is 1,4-dioxane. In other embodiments, the organic solvent is acetonitrile, dimethylsulfoxide (DMSO; CH$_3$—SO—CH$_3$), dimethylformamide (HCON(CH$_3$)$_2$), an aldehyde or a ketone. In still other embodiments, combinations of the above solvents are contemplated. In one embodiment, the aqueous buffer and organic solvent are provided at a ratio of about 1:1.5 to about 1:1, by volume. However, other suitable buffer:solvent ratios will be readily apparent to one of skill in the art. Similarly, other suitable aqueous buffers and organic solvents useful in the process of the invention will be readily apparent to those of skill in the art in view of the specification.

The conversion reaction from SDZ-RAD Isomer B to SDZ-RAD Isomer C may be performed at room temperature, i.e., about 22° C. to about 28° C. Alternatively, the conversion may be performed at lower or higher temperatures, as needed. Typically, conversion is allowed to proceed for about four (4) hours (or longer, as needed or desired) and is stopped by extraction of SDZ-RAD isomer C with a suitable organic solvent.

In one embodiment, the organic solvent used in the extraction is a polar aprotic solvent. In one embodiment, the organic solvent used for extraction is methylene chloride (CH$_2$Cl$_2$). Other suitable solvents, or combinations thereof, will be readily apparent to one of skill in the art in view of the specification.

Isolation of SDZ-RAD Isomer C may be accomplished using preparative chromatography techniques, such as are well known to those of skill in the art. See generally, *Preparative Chromatography*, by R. P. W. Scott, Chrom-Ed Book Series, available online, and *Fundamentals of Preparative and Nonlinear Chromatography*, by Guiochon, G., et al., 1st Academic Press (1994).

SDZ-RAD Isomer C is useful as an immunosuppressive and anti-inflammatory agent in treating, preventing or inhibiting, or in preparing medicaments useful in the treatment, prevention, or inhibition of: transplant rejection, such as kidney, heart, liver, lung, bone marrow, pancreas (islet cells), cornea, small bowel, skin allografts and heart valve xenografts; graft vs. host disease; autoimmune diseases, such as lupus, rheumatoid arthritis, diabetes mellitus, myasthenia gravis and multiple sclerosis; inflammatory diseases, such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveltis.

SDZ-RAD Isomer C also has antitumor, antifungal, and antiproliferative activities. Accordingly, SDZ-RAD Isomer C is useful in treating, preventing or inhibiting, or in preparing medicaments useful in the treatment, prevention, or inhibition of: solid tumors, including fibroids (uterine leiomyoma), sarcomas and carcinomas, such as astrocytomas, prostate cancer, breast cancer, colon cancer, small cell lung cancer, and ovarian cancer; anemia; adult T cell leukemia/lymphoma; mantle cell lymphoma; fungal infections; and hyperproliferative vascular diseases such as restenosis, graft vascular atherosclerosis, cardiovascular disease, cerebral vascular disease, and peripheral vascular disease, such as coronary artery disease, cereberovascular disease, arteriosclerosis, atherosclerosis, nonatheromatous arteriosclerosis, vascular wall damage from cellular events leading toward immune-mediated vascular damage, smooth muscle cell proliferation and intimal thickening following vascular injury, and stroke or multiinfarct dementia. In one embodiment, SDZ-RAD Isomer C is used to treat, prevent or inhibit restenosis following an angioplasty procedure. When used for this purpose, SDZ-Isomer C may be administered prior to, during, or subsequent to the procedure, or any combination of the above.

When administered for the treatment or inhibition or prevention of any of the above diseases or conditions, SDZ-RAD Isomer C may be administered to a mammal orally, parenterally, intravenously, intraperitoneally, intramuscularly, intranasally, intrabronchially, transdermally, topically, intravaginally, or rectally.

Dosage requirements vary according to the route of administration. In one embodiment, daily dosage of SDZ-RAD Isomer C is from approximately 0.1 µg/kg–100 µg/kg, 0.001 mg/kg–25 mg/kg, or approximately 0.01 mg/kg–5 mg/kg. In other embodiments, the dosage will vary depending on the route of administration, the severity of symptoms and the subject being treated (i.e., patient history). Treatment will generally be initiated with small dosages, i.e., dosages less than the optimum dose. Thereafter, the dosage is increased until the optimum effect under the circumstances is reached. Precise dosages may be determined by the administering physician based on general experience and experience with the individual subject or patient to be treated.

Also provided by the invention are pharmaceutical compositions of SDZ-RAD Isomer C according to the invention and one or more pharmaceutically acceptable carriers or excipients. The pharmaceutical carriers or excipients may be solid or liquid. A solid carrier may include one or more substances which may also act as flavoring agents, lubricants, solubilizers, suspending agents, chelating agents, surfactants, fillers, glidants, compression aids, binders, tablet-disintegrating agents, or encapsulating material. In powders, the carrier is a finely divided solid which is in admixture with the finely divided active ingredient, i.e., SDZ-RAD Isomer C. In tablets, the SDZ-RAD Isomer C is mixed with a carrier having the necessary compression properties in suitable proportions and compacted in the shape and size desired. In one embodiment, the powders and tablets contain about 99% or more of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting point waxes and ion exchange resins.

Liquid carriers are used in preparing solutions, suspensions, emulsions, syrups, elixers and pressurized compositions. The active ingredient may be dissolved or suspended in a pharmaceutically acceptable liquid carrier such as water, an organic solvent, a mixture of both, or pharmaceutically acceptable oils or fats. The liquid carrier may contain other suitable pharmaceutical additives such as solubilizers, emulsifiers, buffers, preservatives, sweeteners, flavoring agents, suspending agents, chelating agents, surfactants (e.g., polysorbate 20 or polysorbate 80), thickening agents, colors, viscosity regulators, antioxidants, stabilizers or osmo-regulators. Suitable liquid carriers for oral and parenteral administration include water (containing additives as above, e.g., cellulose derivatives, such as sodium carboxymethyl cellulose solution), alcohols (including monohydric alcohols and polyhydric alcohols, e.g., glycols) and their derivatives, lecithins, and oils (e.g., fractionated coconut oil and arachis oil). For parenteral administration, the carrier may also be an oily ester such as ethyl oleate and isopropyl myristate. Sterile liquid carriers are useful in sterile liquid form compositions for parenteral administration. The liquid carrier for pressurized compositions may be halogenated hydrocarbon or other pharmaceutically acceptable propellant.

Oral formulations of SDZ-RAD Isomer C may include any conventionally used oral forms, including tablets, capsules, buccal forms, troches, lozenges and oral liquids, suspensions or solutions. Capsules may contain mixtures of SDZ-RAD Isomer C with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods, and utilize pharmaceutically acceptable diluents, binding agents, lubricants, disintegrants, surface modifying agents (including surfactants), suspending or stabilizing agents, including but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, dry starches and powdered sugar. Surface modifying agents useful in tablet formulations include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of SDZ-RAD Isomer C. The oral formulation may also include administering the active ingredient in water or fruit juice, containing appropriate solubilizers or emulsifiers as needed.

The pharmaceutical forms of SDZ-RAD Isomer C suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, polyol (e.g., glycerol, propylene glycol and liquid polyethylene glycol), suitable mixtures thereof, and vegetable oils.

The parenteral formulations useful in this invention may be used to produce a dosage form that is suitable for administration by either direct injection or by addition to sterile infusion fluids for intravenous infusion.

In another embodiment, SDZ-RAD Isomer C may be prepared for direct administration to the airways in the form of an aerosol.

Transdermal administration may be accomplished through the use of a transdermal patch containing the active compound and a carrier that is inert to the active compound, is non-toxic to the skin, and allows delivery of the agent for systemic absorption into the blood stream via the skin. Transdermal administration is understood to include all administration across the surface of the body and the inner linings of bodily passages including epithelial and mucosal tissues. Such administrations may be carried out using SDZ-RAD Isomer C, in lotions, creams, foams, patches, suspensions, solutions, and suppositories (rectal and vaginal).

The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices known in the literature are contemplated by the invention.

Suppository formulations may be made from materials known in formulation art, including cocoa butter, with or without the addition of waxes to alter the suppository's melting point, and glycerin. Water soluble suppository bases, such as polyethylene glycols of various molecular weights, may also be used.

SDZ-RAD Isomer C may be formulated for any suitable delivery route and vehicle and assembled in the form of a pharmaceutical pack or kit of parts. Pharmaceutical packs or kits according to the invention are useful in the treatment, inhibition, or prevention of any of the diseases or disorders listed herein, or in the preparation of medicaments useful therefor. In one embodiment, the invention includes a product containing SDZ-RAD Isomer C according to the invention for use in treating a mammal. In another embodiment, the invention includes a pharmaceutical pack containing a course of treatment of a neoplasm for one individual mammal, wherein the pack contains units of SDZ-RAD Isomer C in unit dosage form. In still other embodiments, the above packs/kits include other components, e.g., instructions for dilution, mixing and/or administration of SDZ-RAD Isomer C, containers, syringes, needles, etc. Other such pack/kit components will be readily apparent to one of skill in the art.

The reagents used in the preparation of SDZ-RAD Isomer C may be either commercially obtained or may be prepared by standard procedures described in the literature. The following examples are illustrative of the present invention, but are not a limitation thereof.

EXAMPLE 1

A. Materials and Instruments

SDZ-RAD was obtained from Chemical Development Wyeth-Ayerst Research, Pearl River, N.Y. All solvents were HPLC grade and all other chemicals were analytical reagent or equivalent. The preparative HPLC consisted of two Dynamax™ solvent delivery systems (Model SD-1) and one Dynamax™ absorbance detector (Model UV-1) from Rainin Instrument Company, Inc. (Woburn, Mass.). An automatic speed-vac concentrator (Savant, Model AS 160) was obtained from Savant Instruments, Inc. (Holbrook, N.Y.) and a BUCHI rotary evaporation system (RE 260 and R 124) was obtained from Buchi (Flawil, Switzerland). $^1$H NMR and $^{13}$C data were acquired on 600 MHz Varian Unity Plus spectrometers with a probe temperature of 25° C. Mass spectra were obtained from API 365 mass spectrophotometer from PE Sciex. All samples were prepared and run at ambient temperature.

B. Preparation of Compound

SDZ-RAD (40 mg; 0.042 mmol) was dissolved in 50 mL 40% 0.1 M TEAA buffer pH 8.5 and 60% dioxane. The solution was stirred at room temperature (approximately 22° C. to 28° C.) for 4 hours. The conversion was stopped by 2×50 mL $CH_2Cl_2$ extraction. The organic layer was reduced by rotary evaporation system to dryness. The isolation of compound was performed by BDS-Hypersil-C18 column (250×20 mm) using the mobile phase consisting of 60% dioxane, 40% water with 0.01M TEAA buffer pH 3.9. The flow rate was 12 mL/min. The fraction of isomer C (28.9 min) was collected and extracted with $CH_2Cl_2$ using a separatory funnel. The organic layer was combined and washed with 2×50 mL water and then the organic layer was dried with anhydrous $Na_2SO_4$. The organic solvent was reduced by rotary evaporation to about 1 mL. The product was transferred into a vial and precipitated by adding n-hexane. White powder was obtained by using $N_2$ to blow away the solvent and the vial was put into speed-vac to dry overnight. The purity of the isomer C for each purification step was analyzed by HPLC. ESI mass spectrometry indicates molecular ion $[M+NH_4]^+$ m/e 975.8, which is same as the reference sample of SDZ-RAD.

The NMR sample was prepared in acetone-$d_6$. Table: Proton and Carbon resonance assignment of SDZ-RAD isomer-C (NB # L20156-xxx) in Aceton-d6 at 25° C., 500 MHz ($^{13}$C: 100 MHz)

| C# | δ $^{13}$C major | δ $^1$H major | δ $^{13}$C minor | δ $^1$H minor | $^1$H Correltn | HMBC |
|---|---|---|---|---|---|---|
| 1 | 140.24 | 5.44 | 139.96 | 5.83 | 2, 36 | |
| 2 | 131.87 | 6.23 | 130.94 | 6.26 | 3, 1 | |
| 3 | 133.61 | 6.27 | 134.52 | 6.37 | 4, 2 | |
| 4 | 127.90* | 6.49 | 128.13* | 6.48 | 3, 5 | |
| 5 | 128.14 | 6.16 | 130.38 | 6.25 | 4, 45 | |
| 6 | 139.63 | | 137.02 | | | |
| 7 | 84.16 | 3.77 | 84.60 | 3.88 | 8 | 5, 6, 8, 45, 52 |
| 8 | 44.00 | 2.14; 1.34 | 41.88 | 1.86; 1.72 | 7, 9 | 6, 7 |
| 9 | 74.60 | 3.79 | 73.30 | 3.48 | 8, 10 | 15 |
| 10 | 33.62 | 2.05eq 1.52ax | 36.01 | 1.78eq 1.71ax | 9, 11 | |
| 11 | 35.54 | 1.82eq 1.24ax | 35.28 | 1.75eq 1.23ax | 10, 12 | |
| 12 | 44.08* | 3.24 | 44.15* | 3.17 | 11 | 10, 46 |
| 13 | 210.92 | | 210.43 | | | |
| 15 | 98.77 | | 99.07 | | | |
| 15 (OH) | | 6.07 | | 5.86 | | 12, 13, 15, 16 |
| 16 | 168.84 | | 168.52 | | | |
| 18 | 44.15 | 4.60eq 2.93ax | 39.87 | 4.16eq 3.02ax | 19 | 3.02/ 168.52 |
| 19 | 26.04 | 1.57 1.43 | 25.54 | 1.74 1.44 | 18, 20 | |
| 20 | 21.78* | 1.66 1.51 | 21.69* | 1.79 1.45 | 19, 21 | |
| 21 | 27.09 | 2.28 1.52 | 28.47 | 2.28 1.87 | 20, 22 | |
| 22 | 52.54 | 5.07 | 56.58 | 5.58 | 21 | |
| 23 | 170.66 | | 171.35 | | | |
| 25 | 75.95 | 5.25 | 75.59 | 5.27 | 26, 37 | 23, 26, 28, 37, |

-continued

| C# | δ ¹³C major | δ ¹H major | δ ¹³C minor | δ ¹H minor | ¹H Correltn | HMBC |
|---|---|---|---|---|---|---|
| 26 | 41.46 | 2.80 | 42.84 | 2.83 | 25 | 38, 51 |
|    |       | 2.66 |       | 2.74 |    |    |
| 27 | 208.50 |     | 208.60 |     |    |    |
| 28 | 46.78 | 3.40 | 46.89 | 3.47 | 29, 47 | 47 |
| 29 | 126.08 | 5.31 | 127.55 | 5.52 | 28, 48 | 28, 47 |
| 30 | 137.83 |     | 138.27 |     |    |    |
| 31 | 77.63* | 4.21 | 77.69* | 4.22 |    | 29, 32, 48 |
| 31 (OH) |    | 4.05 |    | 4.05 |    | 30, 31, 32 |
| 32 | 85.96 | 4.16 | 87.57 | 3.82 |    | 31, 32, 34 |
| 33 | 211.79 |    | 212.16 |    |    |    |
| 34 | 42.67 | 2.56 | 40.39 | 2.93 | 35, 49 |    |
| 35 | 40.70 | 1.57(proR) | 41.99 | 1.55(proR) | 34, 36 |    |
|    |       | 1.16(proS) |       | 1.25(proS) |       |    |
| 36 | 37.2 | 2.29 | 34.87 | 2.37 | 1, 35, 50 |    |
| 37 | 34.30 | 1.86 | 34.43 | 1.94 | 38, 51 |    |
| 38 | 40.10 | 1.36 | 39.16 | 1.26 | 37, 39 |    |
|    |       | 1.08 |       | 1.13 |    |    |
| 39 | 33.80* | 1.36 | 33.96* | 1.40 | 38, 40, 44 |    |
| 40 | 37.46 | 2.04 | 37.07 | 2.06 | 39, 41 | 39, 44 |
|    |       | 0.73 |       | 0.69 |    |    |
| 41 | 84.14* | 3.12 | 84.27* | 3.02 | 40, 42 |    |
| 42 | 83.80* | 3.11 | 83.75 | 3.11 | 41, 43 |    |
| 43 | 31.24* | 2.01 | 31.19* | 2.01 | 42, 44 |    |
|    |       | 1.21 |       | 1.21 |    |    |
| 44 | 32.38 | 1.68 | 32.03 | 1.72 | 39, 43 |    |
|    |       | 0.93 |       | 0.91 |    |    |
| 45 | 10.74 | 1.72 | 10.99 | 1.67 | 5 |    |
| 46 | 17.17* | 1.13 | 17.14* | 1.14 | 12 | 11, 12, 13 |
| 47 | 15.96 | 0.95 | 17.02 | 0.09 | 28 |    |
| 48 | 14.56 | 1.83 | 13.42 | 1.75 | 29 |    |
| 49 | 14.32 | 0.93 | 14.94 | 1.02 | 34 |    |
| 50 | 22.04 | 1.03 | 21.43 | 1.06 | 36 |    |
| 51 | 15.63 | 0.87 | 14.56 | 0.93 | 37 | 37 |
| 52 | 56.51 | 3.12 | 56.25 | 3.18 |    |    |
| 53 | 58.04 | 3.27 | 58.35 | 3.26 |    |    |
| 54 | 57.69 | 3.27 | 58.35 | 3.26 |    |    |
| 55 | 72.37* | 3.58* | 72.40* | 3.65* |    |    |
| 56 | 62.58 | 3.58 | 62.58 | 3.58 |    |    |

EXAMPLE 2

Antifungal activity for the compound of this invention was established by evaluation against several strains of fungi. Briefly, the following procedure was used to evaluate such activity. A 96 well microtiter plate was filled (50 µL/well) with RPMI 1640. The compounds to be evaluated were placed in appropriate wells and serial diluted in successive wells to provide several dilutions. The concentrations ranged from 64 to 0.06 mg/mL. An adjusted inoculum of fungi (50 µL) was added to each well and plates were incubated at 35° C. for 24–48 hours. The minimum inhibitory concentration (MIC) is the lowest concentration of compound that completely inhibited growth of organism in the wells. The following table shows the results obtained in this standard pharmacological test procedure. Where the same fungi name is listed more than once, it indicates that more than one strain was evaluated. The compound of this invention is listed in the table's heading as "Compound".

TABLE 1

Antifungal Activity (MIC in µg/mL)

| Yeast/Fungi | ID | Compound | Nystatin | Amphotericin B |
|---|---|---|---|---|
| *Candida albicans* | 94-1 | 0.25 | 2 | 0.125 |
| *Candida albicans* | 1063 | ≦0.06 | 1 | ≦0.06 |
| *Candida albicans* | 1117 | 0.125 | 1 | ≦0.06 |
| *Candida albicans* | ATCC 90028 | 0.125 | 1 | 0.125 |
| *Candida parapsilosis* | 94-9 | 0.125 | 1 | 0.125 |
| *Candida parapsilosis* | 94-8 | 0.125 | 2 | ≦0.06 |
| *Candida parapsilosis* | ATCC 90018 | 0.25 | 2 | ≦0.06 |
| *Candida pseudotropicalis* | ATCC 28838 | ≦0.06 | 1 | ≦0.06 |
| *Candida tropicalis* | 94-14 | 0.125 | 2 | 0.125 |
| *Candida tropicalis* | 94-13 | 0.125 | 1 | 0.125 |
| *Candida krussii* | 94-2 | 0.5 | 1 | 0.125 |
| *Candida lusitaniae* | 94-3 | ≦0.06 | 1 | 0.125 |
| *Candida zeylanoided* | 94-15 | ≦0.06 | 1 | 0.25 |
| *Candida rugosa* | 94-10 | 0.25 | 1 | 0.25 |
| *Aspergillus fumigatus* | ATCC 26933 | 32 | 2 | 0.25 |
| *Aspergillus niger* | ATCC 16404 | 8 | 1 | 0.25 |
| *Aspergillus flavusr* | S506 | 8 | 2 | 0.50 |

The results obtained in this standard pharmacological test procedure demonstrate the effectiveness of SDZ-RAD Isomer C.

All patents, patent applications, articles, publications, and other documents referenced herein are incorporated by reference. One of skill in the art will recognize that minor modifications to the conditions and techniques in the embodiments described herein may be varied without departing from the present invention as defined by the following claims and are encompassed by the invention.

The invention claimed is:

1. An SDZ-RAD Isomer C compound of the structure

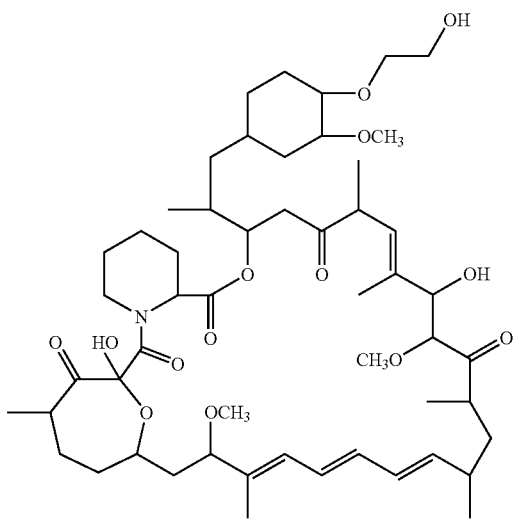

having a purity of greater than 90 wt %.

2. The SDZ-RAD Isomer C according to claim 1, wherein the purity of SDZ-RAD Isomer C is greater than 95 wt %.

3. The SDZ-RAD Isomer C according to claim 1, wherein the purity of SDZ-RAD Isomer C is greater than 99 wt %.

4. SDZ-RAD Isomer C compound of the structure

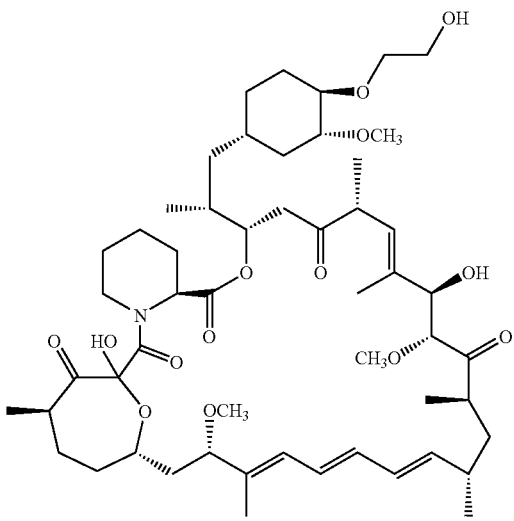

prepared from 42-O-(2-hydroxy)ethyl-rapamycin by
- (a) dissolving 42-O-(2-hydroxy)ethyl-rapamycin in a solution containing an organic solvent and an aqueous buffer, said aqueous buffer having a pH of 4 to 10; and
- (b) extracting the SDZ-RAD Isomer C into an organic solvent.

5. The SDZ-RAD Isomer C prepared according to claim 4, wherein the organic solvent in step (a) is a polar aprotic or dipolar aprotic solvent.

6. The SDZ-RAD Isomer C prepared according to claim 5, wherein the organic solvent in step (a) is acetonitrile or 1,4-dioxane.

7. The SDZ-RAD Isomer C prepared according to claim 6, wherein the organic solvent is 1,4-dioxane.

8. The SDZ-RAD Isomer C prepared according to claim 4, wherein the aqueous buffer has a pH of about 7 to 9.

9. The SDZ-RAD Isomer C prepared according to claim 8, wherein the aqueous buffer has a pH of about 7.5 to 8.5.

10. The SDZ-RAD Isomer C prepared according to claim 9, wherein the aqueous buffer has a pH of about 8.5.

11. The SDZ-RAD Isomer C prepared according to claim 4, wherein the organic solvent in step (b) is a polar aprotic solvent.

12. The SDZ-RAD Isomer C prepared according to claim 11, wherein the organic solvent in step (b) is $CH_2Cl_2$.

13. A pharmaceutical composition comprising SDZ-RAD Isomer C according to claim 1 and a pharmaceutically acceptable carrier or excipient.

14. A pharmaceutical pack containing a course of treatment for a mammal, wherein the pack comprises units of SDZ-RAD Isomer C according to claim 1 in unit dosage form.

15. A pharmaceutical pack containing a course of treatment for a mammal, wherein the pack comprises units of SDZ-RAD Isomer C according to claim 1 in unit dosage form.

* * * * *